(12) United States Patent
Kretz et al.

(10) Patent No.: US 6,924,315 B2
(45) Date of Patent: Aug. 2, 2005

(54) GEMINI GLYCIDYL ETHER ADDUCTS OF POLYHYDROXYALKYL ALKYLENEDIAMINES

(75) Inventors: Christine Peck Kretz, Macungie, PA (US); Michael Edward Ford, Coopersburg, PA (US); Kevin Rodney Lassila, Macungie, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 316 days.

(21) Appl. No.: 10/387,709

(22) Filed: Mar. 13, 2003

(65) Prior Publication Data

US 2004/0180970 A1 Sep. 16, 2004

(51) Int. Cl.$^7$ .......................... B01F 17/16; C08G 65/04; C08G 73/02; C07C 211/00
(52) U.S. Cl. ..................... 516/203; 516/198; 516/204; 106/31.89; 106/401; 528/421; 528/422; 564/1; 564/474; 564/478; 564/487; 564/511
(58) Field of Search ............................... 528/403, 405, 528/421, 422, 425; 106/31.89, 401; 516/198, 203, 204; 564/1, 469, 474, 475, 478, 487, 511

(56) References Cited

U.S. PATENT DOCUMENTS

| | | | |
|---|---|---|---|
| 5,098,478 A | 3/1992 | Krishnan et al. | 106/23 |
| 5,534,197 A | 7/1996 | Scheibel et al. | 510/356 |
| 5,562,762 A | 10/1996 | Mrvos et al. | 106/22 |
| 5,669,984 A | 9/1997 | Scheibel et al. | 134/25.2 |
| 6,746,623 B2 * | 6/2004 | Slone et al. | 252/189 |

FOREIGN PATENT DOCUMENTS

| WO | WO 9519951 | 7/1995 |
|---|---|---|
| WO | WO 9519953 | 7/1995 |

OTHER PUBLICATIONS

M. J. Rosen, Surfactants and Interfacial Phenomena, 2$^{nd}$ Ed., pp. 171–173.
"Kirk Othmer Encyclopedia of Chemical Technology," 4$^{th}$ Ed., vol. 23, pp 477–541.
E. Kissa, "Fluorinated Surfactants," Surfactant Science Series, vol. 50, p 126–7.
J. Schwartz, "The Importance of Low Dynamic Surface Tension in Waterbome Coatings," Journal of Coatings Technology (1992).
W. Wirth, et al., "Mechanisms Controlling Leaf Retention of Agricultural Spray Solutions," Pestic. Sci. 1991, vol. 33, pp. 411–420.
S. W. Medina, et al., "Using Surfactants to Formulate VOC Compliant Waterbased Inks," Am. Ink Maker (1994), 72(2), pp. 32–38.
S. Warwel, et al., "Surfactants from Glucamines and a–epoxides," Tenside Surf. Det. (2001), 38(1), pp. 7–14.
M. L. Fielden, et al., "Sugar–based Tertiary Amino Gemini Surfactants with a Vesicle–to–Micelle Transition in the Endosomal pH Range Mediate Efficient Transfection in vitro," Eur. J. Biochem. 268 (2001), pp. 1269–1279.

* cited by examiner

Primary Examiner—Michael J. Feely
(74) Attorney, Agent, or Firm—Michael Leach

(57) ABSTRACT

The present invention provides compounds useful as surfactants having formula (1), including isomers thereof:

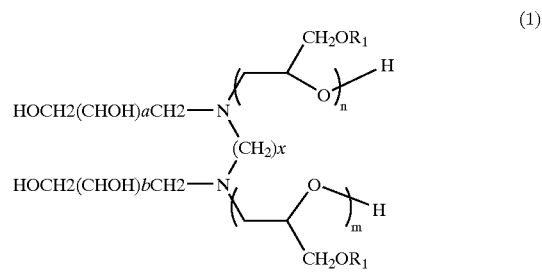

wherein a and b are integers independently selected from about 3 to about 6; x is an integer from about 1 to about 12; (m+n) is from about 1 to about 4; the $R_1$ groups are independently selected from the group consisting of linear, cyclic, and branched alkyl, alkenyl, aryl, and alkylaryl groups having from about $C_3$ to about $C_{30}$ atoms; and when (m+n) is equal to or greater than 2, each $R_1$ may be independently $R_2$ or $R_3$, wherein $R_2$ and $R_3$ are independently selected from the group consisting of linear, cyclic, and branched alkyl, alkenyl, aryl, and alkylaryl groups having from about $C_3$ to about $C_{30}$ atoms. The invention also provides a method for reducing surface tension in a waterborne composition or an industrial process by the incorporation of a surfactant having formula (1) and an aqueous composition comprising a surfactant having formula (1). The invention further provides a product prepared by the reaction of a N,N'-bis(polyhydroxyalkyl)alkylenediamine with a glycidyl ether.

34 Claims, No Drawings

GEMINI GLYCIDYL ETHER ADDUCTS OF POLYHYDROXYALKYL ALKYLENEDIAMINES

FIELD OF THE INVENTION

This invention relates to adducts of N,N'-bis (polyhydroxyalkyl)alkylenediamines with glycidyl ethers, their manufacture, and their use to reduce the surface tension in water-based systems.

BACKGROUND OF THE INVENTION

The ability to reduce the surface tension of water is of great importance in the application of waterborne formulations because decreased surface tension translates to enhanced substrate wetting in actual formulations. Examples of such waterborne compositions include coatings, inks, adhesives, fountain solutions, cleaning compositions, metalworking fluids, and agricultural formulations. Surface tension reduction in water-based systems is generally achieved through the addition of surfactants, resulting in enhanced surface coverage, fewer defects, and more uniform distribution. Equilibrium surface tension performance (EST) is important when the system is at rest. Dynamic surface tension (DST) provides a measure of the ability of a surfactant to reduce surface tension and provide wetting under high speed application conditions.

Surfactants derived from amines such as N-methylglucamine are known for their equilibrium surface tension-reducing capabilities with few of the negative features of traditional nonionic and anionic surfactants.

The importance of a surfactant in achieving low surface tension at low use levels, the ability to affect foaming performance, and the importance of a surfactant in achieving efficient emulsification and solubilization is of considerable industrial importance and is well-appreciated in the art. The fundamental properties and the practical application of surfactants are described in more detail in *Surfactants and Interfacial Phenomena*, 2nd Ed. (Rosen) and in *Kirk Othmer Encyclopedia of Chemical Technology*, 4th Ed., Vol. 23, pp 477–541, which disclosures are incorporated herein by reference.

Many surfactants have the ability to emulsify or solubilize otherwise insoluble organic materials in aqueous media. This emulsification or solubilization occurs at concentrations higher than the critical micelle concentration (CMC). Thus it is desirable for surfactants to have low critical micelle concentrations since this will lead to more efficient surfactant utilization [Rosen, p. 171]. Low critical micelle concentrations are also important because they lead to diminished skin and eye irritation.

The ability of a surfactant to reduce the surface tension of an aqueous formulation is important in promoting substrate wetting. Two parameters that are important when evaluating the relative ability of a surfactant to provide surface tension reduction are the efficiency and effectiveness of the surfactant. The efficiency of a surfactant can be defined by its $pC_{20}$ value:

$$pC_{20} = -\log C_{20}$$

where $C_{20}$ is the concentration in moles/liter of surfactant required to reduce the surface tension of water by 20 dynes/cm. $pC_{20}$ provides a means for comparing the relative amount of surfactant required to obtain a given surface tension reduction. Since the scale is logarithmic, an increase in $pC_{20}$ value of 1 corresponds to a decrease by a factor of 10 in the amount of surfactant required to provide a given surface tension reduction.

The effectiveness of a surfactant can be defined by its limiting surface tension (limiting γ) which is the minimum surface tension observed for an aqueous solution of the surfactant, regardless of surfactant concentration. Effective surfactants can provide wetting under challenging conditions such as those presented by high energy or contaminated substrates.

The foaming characteristics of a surfactant are important because they can help define applications for which the surfactant might be suitable. For example, foam can be desirable for applications such as ore flotation and cleaning. On the other hand, in coatings, graphic arts and adhesive applications, foam is undesirable because it can complicate application and lead to defect formation.

Although equilibrium surface tension reduction efficiency is important for some applications, other applications may require both equilibrium and dynamic surface tension reduction. However, the efficiency with which a surfactant will reduce equilibrium surface tension is not always proportional to the efficiency with which it will reduce dynamic surface tension. A typical example of this low equilibrium surface tension/high dynamic surface tension performance is observed for fluorosurfactants in Kissa's *Fluorinated Surfactants, Surfactant Science Series, Volume* 50, p. 126–7. The dynamic efficiency of a surfactant may be described in a manner similar to that of equilibrium efficiency:

$$pD_{20}^{(x)} = -\log D_{20}^{(x)}$$

where $D_{20}$ is the concentration in moles/liter of surfactant required to reduce the dynamic surface tension of an aqueous solution to 52.1 dynes/cm, or 20 dynes/cm below that of pure water when the measurement is performed using the maximum bubble pressure method at bubble rate x. Similar to comparisons between $pC_{20}$ values, an increase in $pD_{20}^{(x)}$ value of 1 corresponds to a decrease by a factor of 10 in the amount of surfactant required to provide a given dynamic surface tension reduction.

Low dynamic surface tension is of importance in the application of waterborne coatings. Schwartz, J. ["*The Importance of Low Dynamic Surface Tension in Waterborne Coatings*", Journal of Coatings Technology, September 1992] discusses surface tension properties in waterborne coatings, including a discussion of dynamic surface tension in such coatings. Low dynamic surface tension is an important factor in achieving superior film formation in waterborne coatings and preventing defects such as retraction, craters, and foam.

Efficient application of agricultural products is also highly dependent on the dynamic surface tension properties of the formulation. In one article, [Wirth, W.; Storp, S.; Jacobsen, W. "*Mechanisms Controlling Leaf Retention of Agricultural Spray Solutions*"; Pestic. Sci. 1991, 33, 411–420], the relationship between the dynamic surface tension of agricultural formulations and the ability of these formulations to be retained on a leaf was studied. These workers observed a good correlation between retention values and dynamic surface tension, with formulations, which display more effective retention exhibiting low dynamic surface tension.

Low dynamic surface tension is also important in high-speed printing and is discussed in detail in "*Using Surfactants to Formulate VOC Compliant Waterbased Inks*" [Medina, S. W.; Sutovich, M. N. *Am. Ink Maker* 1994, 72 (2), 32–38]. Dynamic surface tension measurements provide an indication of the ability of the surfactant to migrate to a newly created ink/substrate interface to provide wetting during high-speed printing. U.S. Pat. No. 5,098,478 [Krishnan, et al.] teaches that dynamic surface tension in ink compositions for publication gravure printing must be reduced to a level of about 25 to 40 dynes/cm to assure that printability problems will not be encountered. U.S. Pat. No.

5,562,762 [Mrvos, et al.] teaches that low dynamic surface tension is important in ink jet printing.

Low dynamic surface tension is also important in various areas of industrial, institutional, and precision cleaning. The substrate to be cleaned needs to be wetted in order for the soil to be lifted up and separated from the substrate. A similar wetting is necessary for oil and gas applications where oil needs to be separated and removed from narrow pores and cracks in soil and rock.

WO 9519951A1 discloses polyhydroxydiamine compositions having the following structure:

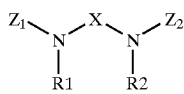

where R1 and R2 are hydrogen, substituted or unsubstituted alkyl, aryl, or alkylaryl groups, X is a bridging group with from 2–200 atoms, and $Z_1$ and $Z_2$ are the same or different alcohol-containing moieties with one or more hydroxyl groups. The compounds are said to be useful in laundry, cleaning, and fabric and personal care compositions.

WO 9519953A1 discloses gemini polyhydroxy fatty acid amides having the following structural formula:

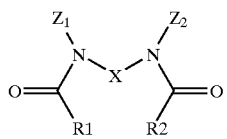

R1 and R2 are hydrocarbyl moieties having 1–21 carbon atoms, X is a bridging group with from 2–200 atoms, and $Z_1$ and $Z_2$ are the same or different alcohol-containing moieties with one or more hydroxyl groups. Although examples of application formulations are provided, there is no discussion of the performance of these molecules.

*Tenside Surf. Det.*, 2001, 38(1), 7–14 [Warwel] describes two families of glucamine-epoxide adducts. Although some molecules are said to exhibit low equilibrium surface tension ($C_{10}$ and $C_{12}$), the molecules are monomeric, not highly soluble, and have varying foam characteristics.

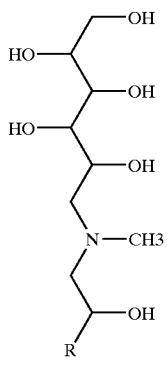

R = C8–C18

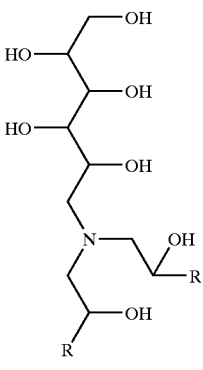

R = C2–C16

Sugar-based tertiary amino gemini surfactants are described in *Eur. J. of Biochem.* 2001, 268(5), 1269–79 and are represented by the formula:

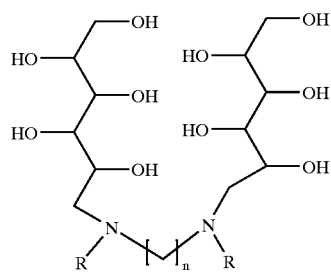

n is 4 or 6 and R is represented by $C_{12}$, $C_{14}$, $C_{16}$, and $C_{18}$ saturated or $C_{18}$ (oleyl) unsaturated alkyl moieties. Although the equilibrium surface tension is described for these surface-active agents, these molecules are not efficient in their equilibrium surface tension reduction.

SUMMARY OF THE INVENTION

The present invention relates to a novel family of surfactants having a combination of low critical micelle concentrations, reduced dynamic and equilibrium surface tension, greater effectiveness with good solubility and moderate foaming. The surfactants of the present invention are adducts of N,N'-bis(polyhydroxyalkyl) alkylenediamines with glycidyl ethers having formula (1), including isomers thereof:

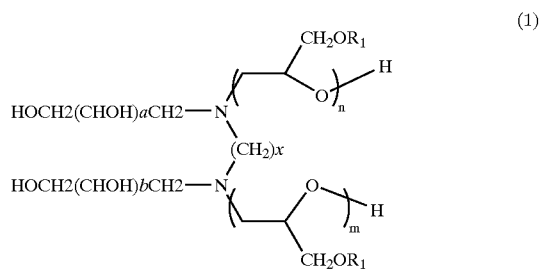

(1)

wherein a and b are integers independently selected from about 3 to about 6; x is an integer from about 1 to about 12; (m+n) is from about 1 to about 4; the $R_1$ groups are independently selected from the group consisting of linear, cyclic, and branched alkyl, alkenyl, aryl, and alkylaryl groups having from about $C_3$ to about $C_{30}$ atoms; and when (m+n) is equal to or greater than 2, each $R_1$ may be independently $R_2$ or $R_3$, wherein $R_2$ and $R_3$ are independently selected from the group consisting of linear, cyclic, and branched alkyl, alkenyl, aryl, and alkylaryl groups having from about $C_3$ to about $C_{30}$ atoms. The invention also relates to a method for reducing surface tension in a waterborne composition or an industrial process by incorporating the subject surfactant into the composition or process and to an aqueous composition comprising the subject surfactant, which composition manifests greater wetting properties in the presence of the surfactant. The invention further provides a product prepared by the reaction of a N,N'-bis (polyhydroxyalkyl) alkylenediamine with a glycidyl ether.

The novel surfactants are useful as emulsifiers or detergents, wetting agents, foaming agents, defoamers, rheology modifiers or associative thickeners, dispersants, and the like. As such, these compounds are useful in applications such as coatings, inks, adhesives, agricultural formulations, fountain solutions, photoresist strippers/developers, soaps, shampoos, and other cleaning compositions. The compounds should also find use in oil-field applications such as enhanced oil recovery, fracturing and stimulation processes, and drilling and cementing operations, and in various wet-processing textile operations, such as dyeing of fibers and fiber scouring and kier boiling.

DETAILED DESCRIPTION OF THE INVENTION

This invention relates to compounds prepared by the reaction of N,N'-bis(polyhydroxyalkyl) alkylenediamines with glycidyl ethers, including isomers thereof, having formula (1):

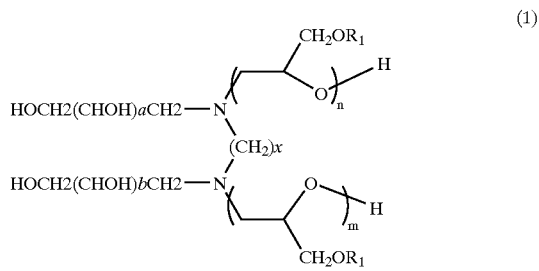

In formula (1), a and b are integers independently selected from about 3 to about 6; x is an integer from about 1 to about 12; (m+n) is from about 1 to about 4; the $R_1$ groups are independently selected from the group consisting of linear, cyclic, and branched alkyl, alkenyl, aryl, and alkylaryl groups having from about $C_3$ to about $C_{30}$ atoms; and when (m+n) is equal to or greater than 2, each $R_1$ may be independently $R_2$ or $R_3$, wherein $R_2$ and $R_3$ are independently selected from the group consisting of linear, cyclic, and branched alkyl, alkenyl, aryl, and alkylaryl groups having from about $C_3$ to about $C_{30}$ atoms.

The compounds of the invention can be prepared by the reaction of a N,N'-bis(polyhydroxyalkyl)alkylenediamine (2) with a glycidyl ether (3), as set out below.

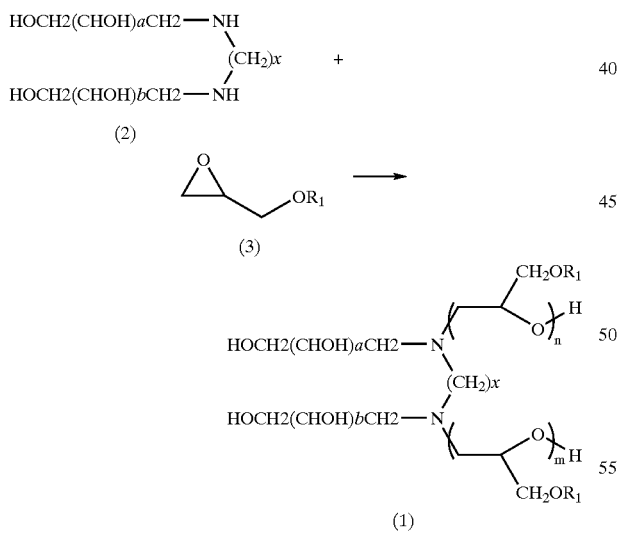

In the N,N'-bis(polyhydroxyalkyl)alkylenediamine (2), a and b are integers independently selected from about 3 to about 6 and x is an integer from about 1 to about 12. In the glycidyl ether (3), $R_1$ is selected from the group consisting of linear, cyclic, and branched alkyl, alkenyl, aryl, alkylaryl groups having from about $C_3$ to about $C_{30}$ atoms, including mixtures thereof. Mixtures of glycidyl ethers may be employed such that the mixture will contain glycidyl ethers having two or more different $R_1$ groups. The ratio of glycidyl ether to N,N'-bis(polyhydroxyalkyl)alkylenediamine is from about 1:1 to about 4:1.

A 1:1 ratio of glycidyl ether to N,N'-bis(polyhydroxyalkyl)alkylenediamine will yield a product having an uncapped amine group (m+n=1). A 2:1 ratio of ratio of glycidyl ether to N,N'-bis(polyhydroxyalkyl) alkylenediamine will yield a product having capped amine groups (m+n=2).

When the ratio of glycidyl ether to N,N'-bis(polyhydroxyalkyl)alkylenediamine is greater than 2:1, opened epoxide rings (hydroxide groups) can react with unopened epoxide rings yielding products with glycidyl chains, $—(CH_2CH(CH_2OR_1)O)—_n$ and $—(CH_2CH(CH_2OR_1)O)—_m$, (m+n>2). Since mixtures of glycidyl ethers can be reacted with the bis(polyhydroxyalkyl) alkylenediamine, each of the glycidyl chains, $—(CH_2CH(CH_2OR_1)O)—n$ and $—(CH_2CH(CH_2OR_1)O)—_m$, can contain glycidyl groups having different $R_1$ groups. More specifically, when (m+n) is greater than 2, each $R_1$ may be independently $R_2$ or $R_3$, wherein $R_2$ and $R_3$ are independently selected from the group consisting of linear, cyclic, and branched alkyl, alkenyl, aryl, and alkylaryl groups having from about $C_3$ to about $C_{30}$ atoms. For example, when (m+n) is 4, the compounds with formula (1) would have the following structure.

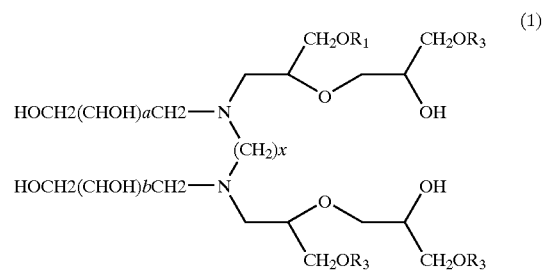

The reaction of N,N'-bis(polyhydroxyalkyl) alkylenediamines with glycidyl ethers will generally yield a mixture of isomers because the amine nitrogen atom can react with either the internal or terminal carbon of the glycidyl ether. The selectivity for each isomer will be influenced by the type of catalyst used (if any) and the reaction conditions. Thus the reaction product may be comprised of one or more of the following isomers:

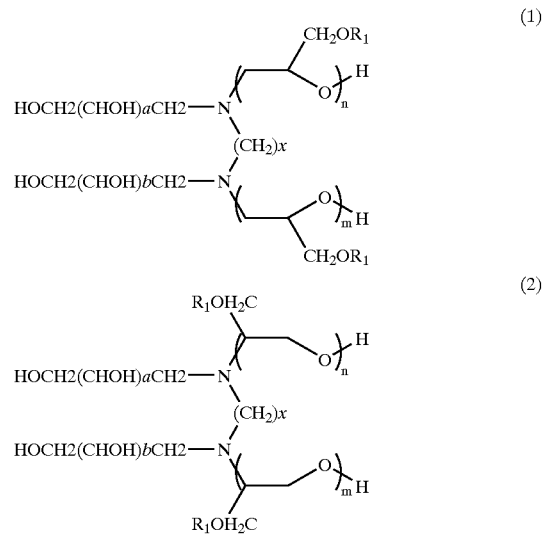

-continued

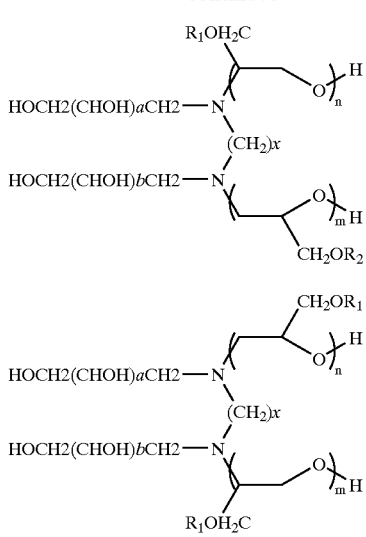

The N,N'-bis(polyhydroxyalkyl) alkylenediamines, with which the glycidyl ethers are reacted, can be prepared by reductive amination of a polyhydroxyalkyl compound, such as a glucose or other suitable mono- or disaccharide, with the desired diamine (see, e.g., Example 1 of WO 9519551).

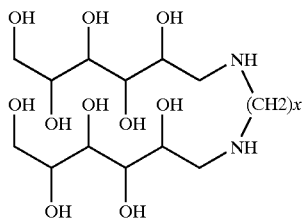

The polyhydroxyalkyl groups, which may be employed in the alkylenediamines, may be independently selected from the group of reducing sugars consisting of glucose, fructose, maltose, lactose, galactose, mannose, and xylose. Other polyhydroxyalkyl groups, which may be used, are glyceraldehydes, high dextrose corn syrup, high fructose corn syrup, and high maltose corn syrup. The preferred polyhydroxyalkyl group is glucose.

The glycidyl ether, with which the N,N'-bis (polyhydroxyalkyl) alkylenediamines are reacted/capped, is an oxirane/ether containing compound which may be represented by the formula below.

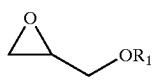

In the glycidyl ether formula above, $R_1$ may be independently a linear, cyclic, or branched alkyl, alkenyl, aryl, or arylalkyl group having from about 3 to about 30 carbon atoms, including mixtures thereof. Preferably $R_1$ is from about 4 to about 18 carbon atoms, and more preferably from about 4 to about 14 carbon atoms. As set out above, mixtures of glycidyl ethers may be employed such that the mixture will contain glycidyl ethers having two or more different $R_1$ groups. Examples of suitable glycidyl ethers include, but are not limited to, ethyl glycidyl ether, butyl glycidyl ether, hexyl glycidyl ether, octyl glycidyl ether, 2-ethylhexyl glycidyl ether, dodecyl glycidyl ether, tridecyl glycidyl ether, tetradecyl glycidyl ether, octadecyl glycidyl ether, phenyl glycidyl ether, cresyl glycidyl ether, and the like, and mixtures thereof. More preferred glycidyl ethers are butyl glycidyl ether, 2-ethylhexyl glycidyl ether, and C12–C14 alkyl glycidyl ethers. The amount of oxirane compound should be from about 1 to about 5 moles based upon the amount of alkylenediamine, preferably from about 1 to about 4 moles, and more preferably from about 1 to about 2 moles, and most preferably 2 moles.

The preferred adducts of the present invention are N,N'-di[2-hydroxy-3-(2-ethyl)hexyloxypropyl]-N,N'-di(1-deoxyglucityl)-1,6-diaminohexane; N,N'-di[2-hydroxy-3-(2-ethyl)hexyloxypropyl]-N,N'-di(1-deoxyglucityl)-1,2-diaminoethane; N,N'di(2-hydroxy-3-butoxypropyl)-N,N'-di(1-deoxyglucityl)-1,6-diaminohexane; N,N'-di(2-hydroxy-3-butoxypropyl)-N,N'-di(1-deoxyglucityl)-1,2-diaminoethane; N,N'-di[2-hydroxy-3-dodecyloxypropyl]-N,N'-di(1-deoxyglucityl)-1,6-diaminohexane; N,N'-di[2-hydroxy-3-tridecyloxypropyl]-N,N'-di(1-deoxyglucityl)-1,6-diaminohexane; N,N'-di[2-hydroxy-3-tetradecyloxypropyl]-N,N'-di(1-deoxyglucityl)-1,6-diaminohexane; N,N'-di[2-hydroxy-3-dodecyloxypropyl]-N,N'-di(1-deoxyglucityl)-1,2-diaminoethane; N,N'-di[2-hydroxy-3-tridecyloxypropyl]-N,N'-di(1-deoxyglucityl)-1,2-diaminoethane; and N,N'-di[2-hydroxy-3-tetradecyloxypropyl]-N,N'-di(1-deoxyglucityl)-1,2-diaminoethane. The more preferred adducts are N,N'-di[2-hydroxy-3-(2-ethyl)hexyloxypropyl]-N,N'-di(1-deoxyglucityl)-1,6-diaminohexane and N,N'-di[2-hydroxy-3-(2-ethyl)hexyloxypropyl]-N,N'-di(1-deoxyglucityl)-1,2-diaminoethane.

To prepare the adducts of the present invention, N,N'-bis (polyhydroxyalkyl) alkylenediamines are reacted (adducted) with the glycidyl ether, optionally in the presence of a solvent, at a temperature sufficiently high so as to provide a convenient reaction rate and sufficiently low so as to prevent significant by-product formation. The reaction temperatures may be in the range from about 50° C. to about 150° C., preferably from about 50° C. to about 130° C., and more preferably from about 60° C. to about 120° C. The optimum conditions will depend upon the reactor configuration, the solvents employed, and other variables. The N,N'-bis (polyhydroxyalkyl) alkylenediamines may be prepared using procedures such as those described in WO 9519951 A1 [Schneibel et al.]. Although the adducting/capping reaction requires no catalyst, a variety of solvents may be used for the reaction. Examples of suitable solvents mixtures include, but may not be limited to, methanol, acetonitrile, ethylene glycol, propylene glycol, water/acetonitrile, water/methanol, and mixtures thereof. The most preferred solvent combination is water/acetonitrile.

When adding glycidyl ethers to the diamine and the catalyst (if any is included), care should be taken to avoid the presence of an excess of unreacted glycidyl ether in the reaction mixture since the reaction is very exothermic and could prove to be very hazardous. The danger of an uncontrollable reaction can be avoided by adding the glycidyl ether in a manner and at a rate such that it reacts as rapidly as it is introduced into the reaction mixture.

The performance properties of these products may be optimized for a specific application by appropriate modification of the structure of the pendant polyhydroxyalkyl group, the diamine chain length, x, and the choice of the substituent, $R_1$, of the glycidyl ether. The interplay among these factors is complex and is not well understood. However, manipulation of these variables yields compounds which are useful as emulsifiers or detergents, wetting agents, foaming agents, defoamers, rheology modifiers or associative thickeners, dispersants, and the like. As such, these compounds will be useful in applications such as coatings, inks, adhesives, agricultural formulations, fountain solutions, photoresist strippers/developers, soaps, shampoos, and other cleaning compositions. The compounds should also find use in oil-field applications such as enhanced oil recovery, fracturing and stimulation processes, and drilling and cementing operations, and in various wet-processing textile operations, such as dyeing of fibers and fiber scouring and kier boiling.

The term "water-based", "waterborne", "aqueous", or "aqueous medium", as used herein, means a solvent or liquid dispersing medium which comprises water, preferably at least 90 wt %, and most preferably at least 95 wt %, water. Obviously, an all water medium is also included.

As set out above, the present invention also provides a method for reducing surface tension in a waterborne composition or an industrial process by the incorporation of a surfactant which comprises utilizing as the surfactant a compound having formula (1), including isomers thereof:

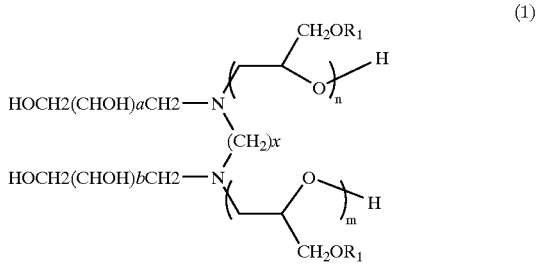
(1)

In formula (1), a and b are integers independently selected from about 3 to about 6; x is an integer from about 1 to about 12; (m+n) is from about 1 to about 4; the $R_1$ groups are independently selected from the group consisting of linear, cyclic, and branched alkyl, alkenyl, aryl, and alkylaryl groups having from about $C_3$ to about $C_{30}$ atoms; and when (m+n) is equal to or greater than 2, each $R_1$ may be independently $R_2$ or $R_3$, wherein $R_2$ and $R_3$ are independently selected from the group consisting of linear, cyclic, and branched alkyl, alkenyl, aryl, and alkylaryl groups having from about $C_3$ to about $C_{30}$ atoms.

The present invention further provides an aqueous composition comprising a surfactant, which composition manifests greater wetting properties in the presence of the surfactant, wherein the surfactant is present in a surfactant effective amount and has formula (I):

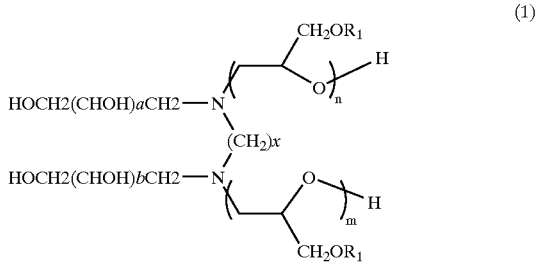
(1)

In formula (1), a and b are integers independently selected from about 3 to about 6; x is an integer from about 1 to about 12; (m+n) is from about 1 to about 4; the $R_1$ groups are independently selected from the group consisting of linear, cyclic, and branched alkyl, alkenyl, aryl, and alkylaryl groups having from about $C_3$ to about $C_{30}$ atoms; and when (m+n) is equal to or greater than 2, each $R_1$ may be independently $R_2$ or $R_3$, wherein $R_2$ and $R_3$ are independently selected from the group consisting of linear, cyclic, and branched alkyl, alkenyl, aryl, and alkylaryl groups having from about $C_3$ to about $C_{30}$ atoms.

The present invention still further provides a product prepared by the reaction of a N,N'-bis(polyhydroxyalkyl) alkylenediamine (2) with a glycidyl ether (3) according to the formula:

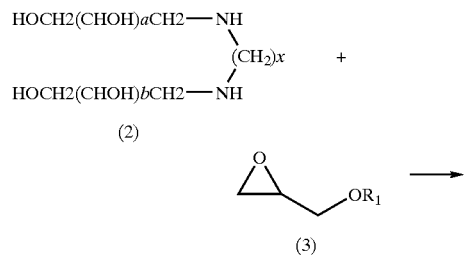

wherein a and b are integers independently selected from about 3 to about 6; x is an integer from about 1 to about 12; $R_1$ is selected from the group consisting of linear, cyclic, and branched alkyl, alkenyl, aryl, alkylaryl groups having from about $C_3$ to about $C_{30}$ atoms, including mixtures thereof; and the ratio of glycidyl ether to N,N'-bis(polyhydroxyalkyl) alkylenediamine is from about 1:1 to about 4:1.

The amount of surfactant that is effective to provide enhanced wetting properties of a water-based, organic compound containing composition may range from 0.00001 wt % to 5 wt %, preferably from 0.0001 wt % to 3 wt %, and most preferably from 0.001 wt % to 3 wt %, based on total weight of the formulation. The most favorable amount will vary from one application to another, depending upon the foam and wetting contributing species in that system.

A typical water-based coating formulation, which includes the surfactants of the invention, is as follows:

| Typical Aqueous-Based Coating Formulation | |
|---|---|
| 0 to 50 wt % | Pigment Dispersant/Grind Resin |
| 0 to 80 wt % | Coloring Pigments/Extender Pigments/Anti-Corrosive Pigments/Other Pigment Types |
| 5 to 99.9 wt % | Water-Borne/Water-Dispersible/Water-Soluble Resins |
| 0 to 30 wt % | Slip Additives/Antimicrobials/Processing Aids/Defoamers |
| 0 to 50 wt % | Coalescing or Other Solvents |
| 0.01 to 10 wt % | Surfactant/Wetting/Flow and Leveling Agents |
| 0.001 to 5 wt % | Glycidyl Ether Adducts of Polyhydroxyalkyl Alkylenediamines |

A typical water-based ink composition, which includes the surfactants of the invention, would comprise the following components in an aqueous medium at 20 to 60% solids:

| Typical Aqueous-Based Ink Composition | |
|---|---|
| 1–50 wt % | Pigment |
| 0 to 50 wt % | Pigment Dispersant/Grind Resin |
| 0 to 50 wt % | Clay base in appropriate resin solution vehicle |
| 5 to 99.9 wt % | Water-borne/water-dispersible/water-soluble resins |
| 0 to 30 wt % | Coalescing Solvents |
| 0.01 to 10 wt % | Surfactant/Wetting Agent |
| 0.01 to 10 wt % | Processing Aids/Defoamers/Solubilizing Agents |

-continued

| Typical Aqueous-Based Ink Composition | |
|---|---|
| 0.001 to 5 wt % | Glycidyl Ether Adducts of Polyhydroxyalkyl Alkylenediamines |

A typical water-based agricultural composition, which includes the surfactants of the invention, would comprise the following components in an aqueous medium at 0.01 to 80% ingredients:

| Typical Aqueous-Based Agricultural Composition | |
|---|---|
| 0.1–50 wt % | Pesticide or Plant Growth Modifying Agent |
| 001 to 10 wt % | Surfactant |
| 0 to 5 wt % | Dyes |
| 0 to 20 wt % | Thickeners/Stabilizers/Co-surfactants/Gel Inhibitors/Defoamers |
| 0 to 25 wt % | Antifreeze |
| 0.001 to 50 wt % | Glycidyl Ether Adducts of Polyhydroxyalkyl Alkylenediamines |

A typical fountain solution composition for planographic printing, which includes the surfactants of the invention, would comprise the following components:

| Typical Fountain Solution for Planographic Printing | |
|---|---|
| 0.05 to 10 wt % | Film formable, water soluble macromolecule |
| 1 to 25 wt % | Alcohol, glycol, or polyol with 2–12 carbon atoms, water soluble or can be made to be water soluble |
| 0.01 to 20 wt % | Water soluble organic acid, inorganic acid, or a salt of these |
| 30 to 70 wt % | Water |
| 0.001 to 5 wt % | Glycidyl Ether Adducts of Polyhydroxyalkyl Alkylenediamines |

A typical hard surface cleaner, which includes the surfactants of the invention, would comprise the following components:

| Typical Hard Surface Cleaner | |
|---|---|
| 0 to 5 wt % | Anionic Surfactant |
| 0 to 5 wt % | Nonionic surfactant |
| 0 to 3 wt % | Carboxylate salt |
| 1 to 5 wt % | Glycol ether |
| 0.5 to 3 wt % | Buffering agents |
| 80 to 95 wt % | Water |
| 0.001 to 5 wt % | Glycidyl Ether Adducts of Polyhydroxyalkyl Alkylenediamines |

A typical water-based photoresist developer or electronic cleaning composition, which includes the surfactants of the invention, would comprise the following components:

| Typical Aqueous-Based Photoresist Developer Composition | |
|---|---|
| 0.1 to 3 wt % | Tetramethylammonium hydroxide |
| 0 to 4 wt % | Phenolic resin |
| 88 to 99.9 wt % | Water |
| 10–5000 ppm | Glycidyl Ether Adducts of Polyhydroxyalkyl Alkylenediamines |

Throughout this disclosure, the applicant will suggest various theories or mechanisms by which applicant believes the present methods function. While applicant may offer various mechanisms to explain the present invention, applicant does not wish to be bound by theory. These theories are suggested to better understand the present invention but are not intended to limit the effective scope of the claims.

Throughout this application, various publications have been referenced. The disclosures in these publications are incorporated herein by reference in order to more fully describe the state of the art.

The present invention is further illustrated by the following examples, which are presented for purposes of demonstrating, but not limiting, the preparation of the compounds and compositions of this invention.

EXAMPLES

Examples 1–6

These examples illustrate the preparation of the glycidyl ether derivatives of N,N'-di(1-deoxyglucityl) alkylenediamines of the invention. The preparation of the 2-ethylhexyl adduct with N,N'-di(1-deoxyglucityl) ethylenediamine will be used for illustration. To a 3-necked 500 mL round-bottomed flask equipped with a stir bar, reflux condenser, addition funnel, and thermocouple was added N,N'-di(1-deoxyglucityl)ethylenediamine (3.65 g, 8.2 mmol, 1 eq.) which was prepared via a slightly modified version of the procedure described in WO 9519551 A1. To the diamine was added 50 g $CH_3CN$ and 20 g $H_2O$ and the mixture was stirred under nitrogen while heating to 60° C. with a heating mantle. To the reaction mixture was added 2-ethylhexyl glycidyl ether (Epodil® 746, 3.05 g, 16.4 mmol, 2 eq.) in a dropwise fashion over 15 minutes. Once all of the glycidyl ether was added, the reaction mixture was heated to 78° C. for a total of 9 hours. The reaction mixture was cooled to 60° C. and the solvent was removed at this temperature at ambient pressure and then under vacuum. The product was identified as the desired adduct via $^{13}C$ NMR and matrix assisted laser desorption/ionization (MALD/I) mass spectrometry. Additional adducts of N,N'-di(1-deoxyglucityl)alkylenediamines were prepared and characterized using procedures similar to that above. Some of the adducts that were prepared and their designations are shown in Table 1.

TABLE 1

Glycidyl Ether Adducts of Polyhydroxyalkyl Alkylenediamines

| Example | Spacer Length (x) | Capping Group | Designation |
|---|---|---|---|
| Example 1 | 2 | BGE | DGEDA/2BGE |
| Example 2 | 2 | EHGE | DGEDA/2EHGE |
| Example 3 | 2 | LTDGE | DGEDA/2LTDGE |
| Example 4 | 6 | BGE | DGHMDA/2BGE |

TABLE 1-continued

Glycidyl Ether Adducts of Polyhydroxyalkyl Alkylenediamines

| Example | Spacer Length (x) | Capping Group | Designation |
|---|---|---|---|
| Example 5 | 6 | EHGE | DGHMDA/2EHGE |
| Example 6 | 6 | LTDGE | DGHMDA/2LTDGE |

The preferred starting diamines used for the preparation of these materials have the following structures:

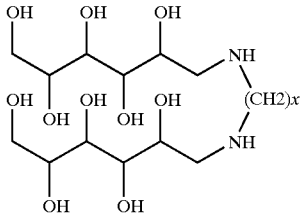

where x=2 or 6 corresponding, respectively, to the ethylenediamine (EDA) or hexamethylenediamine (H MDA) derivatives.

The preferred glycidyl ether starting materials have the following structures and designations:

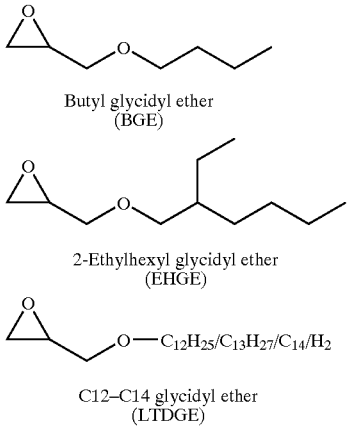

Butyl glycidyl ether (BGE)

2-Ethylhexyl glycidyl ether (EHGE)

C12–C14 glycidyl ether (LTDGE)

The names of the glycidyl ether adducts of polyhydroxyalkyl alkylenediamines set out in Table 1 are as follows:

DGHMDA/2EHGE: N,N'-di[2-hydroxy-3-(2-ethyl) hexyloxypropyl]-N,N'-di(1-deoxyglucityl)-1,6-diaminohexane.

DGEDA/2EHGE: N,N'-di[2-hydroxy-3-(2-ethyl) hexyloxypropyl]-N,N'-di(1-deoxyglucityl)-1,2-diaminoethane.

DGHMDA/2BGE: N,N'-di(2-hydroxy-3-butoxypropyl)-N,N'-di(1-deoxyglucityl)-1,6-diaminohexane.

DGEDA/2BGE: N,N'-di(2-hydroxy-3-butoxypropyl)-N,N'-di(1-deoxyglucityl)-1,2-diaminoethane.

DGHMDA/2LTDGE: Since the glycidyl ether from which this material is derived is a mixture of the glycidyl ethers of $C_{12}$, $C_{13}$, and $C_{14}$ alcohols, this material is a mixture of:

N,N'-di[2-hydroxy-3-dodecyloxypropyl]-N,N'-di(1-deoxyglucityl)-1,6-diaminohexane;

N,N'-di[2-hydroxy-3-tridecyloxypropyl]-N,N'-di(1-deoxyglucityl)-1,6-diaminohexane; and N,N'-di[2-hydroxy-3-tetradecyloxypropyl]-N,N'-di(1-deoxyglucityl)-1,6-diaminohexane.

DGEDA/2LTDGE: Since the glycidyl ether from which this material is derived is a mixture of the glycidyl ethers of $C_{12}$, $C_{13}$, and $C_{14}$ alcohols, this material is a mixture of:

N,N'-di[2-hydroxy-3-dodecyloxypropyl]-N,N'-di(1-deoxyglucityl)-1,2-diaminoethane;

N,N'-di[2-hydroxy-3-tridecyloxypropyl]-N,N'-di(1-deoxyglucityl)-1,2-diaminoethane; and N,N'-di[2-hydroxy-3-tetradecyloxypropyl]-N,N'-di(1-deoxyglucityl)-1,2-diaminoethane.

Examples 7–12

Equilibrium surface tensions were determined using a Kruss K-12 tensiometer with a platinum Wilhelmy plate, maintaining the temperature at 25±1° C. by means of a constant temperature circulating bath. Results reported are averages of 10 measurements over a 10-minute period having a standard deviation of less than 0.01 dyne/cm. In many instances the solutions took hours to reach equilibrium. This data was used to determine critical micelle concentrations, $pC_{20}$ values, and limiting surface tensions and is listed in Table 2.

TABLE 2

Equilibrium Surfactant Data for Glycidyl Ether Adducts of Polyhydroxyalkyl Alkelenediamines

| Compound | Critical Micelle Concentration (CMC) | | $pC_{20}$ | Limiting $\gamma$ |
|---|---|---|---|---|
| | mol/L | wt % | | |
| DGEDA/2BGE | $4.00 \times 10^{-3}$ | 0.0026 | 3.74 | 26.0 |
| DGEDA/2EHGE | $2.52 \times 10^{-5}$ | 0.00002 | 5.27 | 26.0 |
| DGEDA/2LTDGE | $3.63 \times 10^{-4}$ | 0.00033 | 6.28 | 25.4 |
| DGHMDA/2BGE | $1.23 \times 10^{-2}$ | 0.0087 | 4.36 | 26.4 |
| DGHMDA/2EHGE | $7.35 \times 10^{-5}$ | 0.00006 | 5.65 | 27.2 |
| DGHMDA/2LTDGE | $8.26 \times 10^{-4}$ | 0.00079 | 6.35 | 27.8 |

Several measures of equilibrium surface tension are given in Table 2. The first measure, CMC, should be coupled with the third, limiting surface tension. While CMC indicates the amount of surfactant needed to reach the limiting surface tension, the limiting $\gamma$ value provides a measure of the effectiveness or the lowest equilibrium surface tension value that a surfactant can reach. Some of the practical benefits of a low CMC are that less surfactant is required to reduce the surface tension of a formulation (enhancing its wetting properties) and less surfactant will be needed to stabilize emulsions. The last measure of equilibrium surface tension, $pC_{20}$, indicates the concentration of surfactant required to reduce the equilibrium surface tension by 20 dynes/cm, with higher $pC_{20}$ values corresponding to lower concentrations of surfactant required to obtain a solution with a 52 dynes/cm surface tension. This data is also a measure of the effectiveness of a surfactant. For the examples in Table 2, the glycidyl ether adducts of the invention demonstrate either low CMCs, low limiting surface tension or high $pC_{20}$ values, or some combination of all three.

Examples 13–18

The foaming characteristics of these new materials were determined using a slight modification of the Ross-Miles foam test (*Am. Soc. For Testing Materials*, Method D1173–53, Philadelphia, Pa., 1953) for solutions of 0.01 wt % surfactant in water. The data are shown in Table 3.

TABLE 3

Foam Stability Data

| Example | Compound | Initial Foam Height (cm) | Final Foam Height (cm) at 300 Sec | Time to 0 foam (sec) |
|---|---|---|---|---|
| 13 | DGEDA/2BGE | 3.5 | 0 | 30 |
| 14 | DGEDA/2EHGE | 2.8 | 1.4 | >300 |
| 15 | DGEDA/2LTDGE | 1.0 | 0.5 | >300 |
| 16 | DGHMDA/2BGE | 2.0 | 0 | 30 |
| 17 | DGHMDA/2EHGE | 1.5 | 1.5 | >300 |
| 18 | DGHMDA/2LTDGE | 0.5 | 0.5 | >300 |

These results show an increase in foam stability with an increase in hydrophobe length (Examples 17 and 18 vs. 16, Examples 14 and 15 vs. 13). This data demonstrates that a range of foam performance may be obtained, depending upon the glycidyl ether capping group. While applications such as coatings, inks, and adhesives require low foam or foam that dissipates quickly, other applications such as cleaning or ore floatation require a controlled amount of foam to be present and to persist. Therefore, the glycidyl ether surfactants of the invention will be likely to be used for a wide range of applications.

Examples 19–24

An additional benefit that the surfactants of the invention offer is the reduction of dynamic surface tension. Solutions in distilled water of the surfactants of the invention were prepared. Their dynamic surface tensions were measured using the maximum bubble pressure method, and these data were used to determine the values provided in Table 4. The maximum bubble pressure method of measuring surface tension is described in *Langmuir* 1986, 2, 428–432, which is incorporated by reference. These data provide information about the performance of a surfactant at conditions close to equilibrium (0.1 bubbles/sec) through high surface creation rates or dynamic conditions (20 bubbles/sec). In a practical sense, high surface creation rates refer to rapid processes such as a spray or roller-applied coating, a high speed printing operation, or the rapid application of an agricultural product or a cleaner.

TABLE 4

Dynamic Surface Tension Data

| Example | Compound | $pD_{20}^{(0.1)}$ | Limiting γ | | Dynamic surface tension (0.1% solution) | |
|---|---|---|---|---|---|---|
| | | | (0.1 b/s) | (20 b/s) | (1 b/s) | (6 b/s) |
| 19 | DGEDA/2BGE | 2.57 | 42 | 51 | 60 | 63 |
| 20 | DGEDA/2EHGE | 5.18 | 24 | 41 | 32 | 50 |
| 21 | DGEDA/2LTDGE | 2.30 | 39 | 66 | 72 | 72 |
| 22 | DGHMDA/2BGE | 3.01 | 40 | 45 | 53 | 54 |
| 23 | DGHMDA/2EHGE | 5.61 | 24 | 54 | 36 | 60 |
| 24 | DGHMDA/2LTDGE | 2.44 | 44 | 71 | 65 | 72 |

The ability of the surfactants of the invention to reduce dynamic surface tension is shown by the limiting surface tension values, limiting γ, as well as the dynamic surface tension values at 0.1 wt % (a common concentration for surfactant evaluation). This data as well as the $pD_{20}^{(0.1)}$ values reveals that a wide range of dynamic surface tension reduction is possible with this family of molecules providing differing surfactants for strong (Examples 20 and 23), moderate (Examples 19 and 22), and low (Examples 21 and 24) surface tension reduction of an aqueous solution or a formulation. Depending upon the mode of application of a formulation and the substrate to be wetted (brush application of an industrial coating, spray application of an industrial cleaner, roller application of an adhesive), surfactants that provide such a wide range of dynamic surface tension reduction will be commercially useful.

This invention provides a family of novel surfactants with properties that will make them of value in a wide range of industrial and commercial applications. These include waterbased coatings, inks, adhesives, agricultural formulations, aqueous and non-aqueous cleaning compositions, personal care applications, and formulations for textile processing and oilfield applications.

We claim:

1. A compound having formula (1), including isomers thereof:

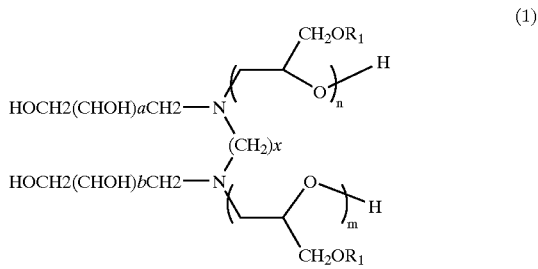

wherein a and b are integers independently selected from about 3 to about 6; x is an integer from about 1 to about 12; (m+n) is from about 1 to about 4; the $R_1$ groups are independently selected from the group consisting of linear, cyclic, and branched alkyl, alkenyl, aryl, and alkylaryl groups having from about $C_3$ to about $C_{30}$ atoms; and when (m+n) is equal to or greater than 2, each $R_1$ may be independently $R_2$ or $R_3$, wherein $R_2$ and $R_3$ are independently selected from the group consisting of linear, cyclic, and branched alkyl, alkenyl, aryl, and alkylaryl groups having from about $C_3$ to about $C_{30}$ atoms.

2. The compound of claim 1, wherein the $HOH_2C(CHOH)_aH_2C$— and $HOH_2C(CHOH)_bH_2C$— moieties are independently derived from the group consisting of glucose, fructose, maltose, lactose, galactose, mannose, xylose, glyceraldehydes, high dextrose corn syrup, high fructose corn syrup, and high maltose corn syrup moieties.

3. The compound of claim 2, wherein the $HOH_2C(CHOH)_aH_2C$— and $HOH_2C(CHOH)_bH_2C$— moieties are derived from glucose moieties.

4. The compound of claim 1, wherein a and b are 4.

5. The compound of claim 1, wherein x is 2 or 6.

6. The compound of claim 1, wherein (m+n) is 1 or 2.

7. The compound of claim 1, wherein $R_1$ is independently selected from the group consisting of butyl, 2-ethylhexyl, and C12–C14 alkyl.

8. The compound of claim 1, wherein the compound is selected from the group consisting of N,N'-di[2-hydroxy-3-(2-ethyl)hexyloxypropyl]-N,N'-di(1-deoxyglucityl)-1,6-diaminohexane; N,N'-di[2-hydroxy-3-(2-ethyl)hexyloxypropyl]-N,N'-di(1-deoxyglucityl)-1,2-diaminoethane; N,N'di(2-hydroxy-3-butoxypropyl)-N,N'-di(1-deoxyglucityl)-1,6-diaminohexane; N,N'-di(2-hydroxy-3-butoxypropyl)-N,N'-di(1-deoxyglucityl)-1,2-diaminoethane; N,N'-di[2-hydroxy-3-dodecyloxypropyl]-N,N'-di(1-deoxyglucityl)-1,6-diaminohexane; N,N'-di[2-hydroxy-3-tridecyloxypropyl]-N,N'-di(1-deoxyglucityl)-1,6-diaminohexane; N,N'-di[2-hydroxy-3-tetradecyloxypropyl]-N,N'-di(1-deoxyglucityl)-1,6- diaminohexane; N,N'-di[2-hydroxy-3-dodecyloxypropyl]-N,N'-di(1-deoxyglucityl)-1,2-diaminoethane; N,N'-di[2-hydroxy-3-tridecyloxypropyl]-N,N'-di(1-deoxyglucityl)-1,2-diaminoethane; and N,N'-di[2-hydroxy-3-tetradecyloxypropyl]-N,N'-di(1-deoxyglucityl)-1,2-diaminoethane.

9. The compound of claim 8, wherein the compound is N,N'-di[2-hydroxy-3-(2-ethyl)hexyloxypropyl]-N,N'-di(1-deoxyglucityl)-1,6-diaminohexane or N,N'-di[2-hydroxy-3-(2-ethyl)hexyloxypropyl]-N,N'-di(1-deoxyglucityl)-1,2-diaminoethane.

10. A method for reducing surface tension in a waterborne composition or an industrial process by the incorporation of a surfactant which comprises utilizing as the surfactant a compound having formula (1), including isomers thereof:

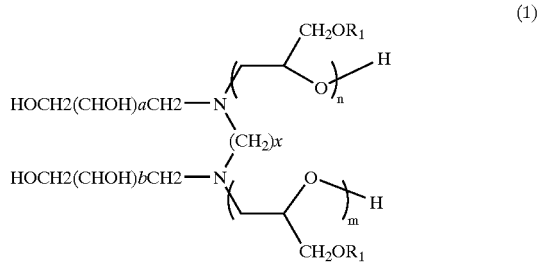

(1)

wherein a and b are integers independently selected from about 3 to about 6; x is an integer from about 1 to about 12; (m+n) is from about 1 to about 4; the $R_1$ groups are independently selected from the group consisting of linear, cyclic, and branched alkyl, alkenyl, aryl, and alkylaryl groups having from about $C_3$ to about $C_{30}$ atoms; and when (m+n) is equal to or greater than 2, each $R_1$ may be independently $R_2$ or $R_3$, wherein $R_2$ and $R_3$ are independently selected from the group consisting of linear, cyclic, and branched alkyl, alkenyl, aryl, and alkylaryl groups having from about $C_3$ to about $C_{30}$ atoms.

11. The method of claim 10, wherein the $HOH_2C(CHOH)_a H_2C$— and $HOH_2C(CHOH)_b H_2C$— moieties are independently derived from the group consisting of glucose, fructose, maltose, lactose, galactose, mannose, xylose, glyceraldehydes, high dextrose corn syrup, high fructose corn syrup, and high maltose corn syrup moieties.

12. The method of claim 11, wherein the $HOH_2C(CHOH)_a H_2C$— and $HOH_2C(CHOH)_b H_2C$— moieties are derived from glucose moieties.

13. The method of claim 10, wherein a and b are 4.

14. The method of claim 10, wherein x is 2 or 6.

15. The method of claim 10, wherein (m+n) is 1 or 2.

16. The method of claim 10, wherein $R_1$ is independently selected from the group consisting of butyl, 2-ethylhexyl, and C12–C14 alkyl.

17. The method of claim 10, wherein the compound is selected from the group consisting of N,N'-di[2-hydroxy-3-(2-ethyl)hexyloxypropyl]-N,N'-di(1-deoxyglucityl)-1,6-diaminohexane; N,N'-di[2-hydroxy-3-(2-ethyl)hexyloxypropyl]-N,N'-di(1-deoxyglucityl)-1,2-diaminoethane; N,N'di(2-hydroxy-3-butoxypropyl)-N,N'-di(1-deoxyglucityl)-1,6-diaminohexane; N,N'-di(2-hydroxy-3-butoxypropyl)-N,N'-di(1-deoxyglucityl)-1,2-diaminoethane; N,N'-di[2-hydroxy-3-dodecyloxypropyl]-N,N'-di(1-deoxyglucityl)-1,6-diaminohexane; N,N'-di[2-hydroxy-3-tridecyloxypropyl]-N,N'-di(1-deoxyglucityl)-1,6-diaminohexane; N,N'-di[2-hydroxy-3-tetradecyloxypropyl]-N,N'-di(1-deoxyglucityl)-1,6-diaminohexane; N,N'-di[2-hydroxy-3-dodecyloxypropyl]-N,N'-di(1-deoxyglucityl)-1,2-diaminoethane; N,N'-di[2-hydroxy-3-tridecyloxypropyl]-N,N'-di(1-deoxyglucityl)-1,2-diaminoethane; and N,N'-di[2-hydroxy-3-tetradecyloxypropyl]-N,N'-di(1-deoxyglucityl)-1,2-diaminoethane.

18. The compound of claim 17, wherein the compound is N,N'-di[2-hydroxy-3-(2-ethyl)hexyloxypropyl]-N,N'-di(1-deoxyglucityl)-1,6-diaminohexane or N,N'-di[2-hydroxy-3-(2-ethyl)hexyloxypropyl]-N,N'-di(1-deoxyglucityl)-1,2-diaminoethane.

19. An aqueous composition comprising a surfactant, which composition manifests greater wetting properties in the presence of the surfactant, wherein the surfactant is present in a surfactant effective amount and has formula (1), including isomers thereof:

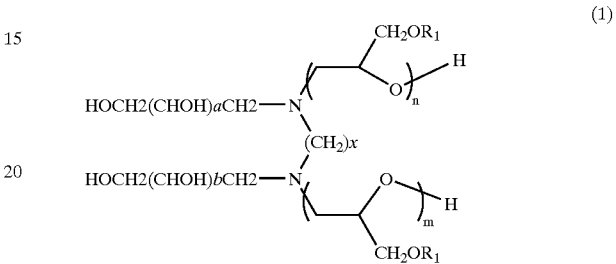

(1)

wherein a and b are integers independently selected from about 3 to about 6; x is an integer from about 1 to about 12; (m+n) is from about 1 to about 4; the $R_1$ groups are independently selected from the group consisting of linear, cyclic, and branched alkyl, alkenyl, aryl, and alkylaryl groups having from about $C_3$ to about $C_{30}$ atoms; and when (m+n) is equal to or greater than 2, each $R_1$ may be independently $R_2$ or $R_3$, wherein $R_2$ and $R_3$ are independently selected from the group consisting of linear, cyclic, and branched alkyl, alkenyl, aryl, and alkylaryl groups having from about $C_3$ to about $C_{30}$ atoms.

20. The composition of claim 19, wherein the $HOH_2C(CHOH)_a H_2C$— and $HOH_2C(CHOH)_b H_2C$— moieties are independently derived from the group consisting of glucose, fructose, maltose, lactose, galactose, mannose, xylose, glyceraldehydes, high dextrose corn syrup, high fructose corn syrup, and high maltose corn syrup moieties.

21. The composition of claim 20, wherein the $HOH_2C(CHOH)_a H_2C$— and $HOH_2C(CHOH)_b H_2C$— moieties are derived from glucose moieties.

22. The composition of claim 19, wherein a and b are 4.

23. The composition of claim 19, wherein x is 2 or 6.

24. The composition of claim 19, wherein (m+n) is 1 or 2.

25. The composition of claim 19, wherein $R_1$ and $R_2$ are independently selected from the group consisting of butyl, 2-ethylhexyl, and C12–C14 alkyl.

26. The compound of claim 19, wherein the compound is selected from the group consisting of N,N'-di[2-hydroxy-3-(2-ethyl)hexyloxypropyl]-N,N'-di(1-deoxyglucityl)-1,6-diaminohexane; N,N'-di[2-hydroxy-3-(2-ethyl)hexyloxypropyl]-N,N'-di(1-deoxyglucityl)-1,2-diaminoethane; N,N'di(2-hydroxy-3-butoxypropyl)-N,N'-di(1-deoxyglucityl)-1,6-diaminohexane; N,N'-di(2-hydroxy-3-butoxypropyl)-N,N'-di(1-deoxyglucityl)-1,2-diaminoethane; N,N'-di[2-hydroxy-3-dodecyloxypropyl]-N,N'-di(1-deoxyglucityl)-1,6-diaminohexane; N,N'-di[2-hydroxy-3-tridecyloxypropyl]-N,N'-di(1-deoxyglucityl)-1,6-diaminohexane; N,N'-di[2-hydroxy-3-tetradecyloxypropyl]-N,N'-di(1-deoxyglucityl)-1,6-diaminohexane; N,N'-di[2-hydroxy-3-dodecyloxypropyl]-N,N'-di(1-deoxyglucityl)-1,2-diaminoethane; N,N'-di[2-hydroxy-3-tridecyloxypropyl]-N,N'-di(1-deoxyglucityl)-1,2-diaminoethane; and N,N'-di[2-hydroxy-3- tetradecyloxypropyl]-N,N'-di(1-deoxyglucityl)-1,2-diaminoethane.

27. The compound of claim 26, wherein the compound is N,N'-di[2-hydroxy-3-(2-ethyl)hexyloxypropyl]-N,N'-di(1-deoxyglucityl)-1,6-diaminohexane or N,N'-di[2-hydroxy-3-(2-ethyl)hexyloxypropyl]-N,N'-di(1-deoxyglucityl)-1,2-diaminoethane.

28. The composition of claim 19, comprising an aqueous medium and 30 to 80 wt % of a coating composition, wherein said coating composition comprises 0.001 to 5 wt % of the surfactant of formula (1) and further comprises the following components to form an aqueous coating composition:
   (a) 0 to 50 wt % of at least one of a pigment dispersant and a grind resin;
   (b) 0 to 80 wt % of at least one of coloring pigments, extender pigments, anti-corrosive pigments, and other pigments;
   (c) 5 to 99.9 wt % of at least one of a water-borne resin, a water-dispersible resin, and a water-soluble resin;
   (d) 0 to 30 wt % of at least one of slip additives, anti-microbials, processing aids, and defoamers;
   (e) 0 to 50 wt % of at least one of coalescing solvents and other solvents; and
   (f) 0.01 to 10 wt % of at least one of a surfactant, a wetting agent, a flow agent, and a leveling agent.

29. The composition of claim 19, comprising an aqueous medium and 20 to 60 wt % of an ink composition, wherein said ink composition comprises 0.001 to 5 wt % of the surfactant of formula (1) and further comprises the following components to form an aqueous ink composition:
   (a) 1 to 50 wt % of pigment;
   (b) 0 to 50 wt % of at least one of a pigment dispersant and a grind resin;
   (c) 0 to 50 wt % of a clay base in an appropriate resin solution vehicle;
   (d) 5 to 99.9 wt % of at least one of a water-borne resin, a water-dispersible resin, and a water-soluble resin;
   (e) 0 to 30 wt % of coalescing solvents;
   (f) 0.01 to 10 wt % of at least one of a surfactant and a wetting agent; and
   (g) 0.01 to 10 wt % of at least one of processing aids, defoamers, and solubilizing agents.

30. The composition of claim 19, comprising an aqueous medium and 0.1 to 80 wt % of an agricultural composition, wherein said agricultural composition comprises 0.001 to 50 wt % of the surfactant of formula (1) and further comprises the following components to form an aqueous agricultural composition:
   (a) 0.1 to 50 wt % of at least one of a pesticide and a plant growth modifying agent;
   (b) 0.01 to 10 wt % of surfactant;
   (c) 0 to 5 wt % of dyes;
   (d) 0 to 20 wt % of at least one of thickeners, stabilizers, co-surfactants, gel inhibitors, and defoamers; and
   (e) 0 to 25 wt % of antifreeze.

31. The composition of claim 19, comprising 0.001 to 5 wt % of the surfactant of formula (1), 30 to 70 wt % of water, and further comprising the following components to form a fountain solution:
   (a) 0.5 to 10 wt % of a film formable, water soluble macromolecule;
   (b) 1 to 25 wt % of at least one of an alcohol, a glycol, and a polyol with 2 to 12 carbon atoms, which is water soluble or can be made to be water soluble; and
   (c) 0.01 to 20 wt % of a least one of a water-soluble organic acid or salt thereof, and a water-soluble inorganic acid or salt thereof.

32. The composition of claim 19, comprising 0.001 to 5 wt % of the surfactant of formula (1), 80 to 95 wt % of water, and further comprising the following components to form a hard surface cleaner composition:
   (a) 0 to 5 wt % of an anionic surfactant;
   (b) 0 to 5 wt % of a nonionic surfactant;
   (c) 0 to 3 wt % of a carboxylate salt;
   (d) 1 to 5 wt % of a glycol ether; and
   (e) 0.5 to 3 wt % of buffering agents.

33. The composition of claim 19, comprising 10–5,000 ppm of the surfactant of formula (1), 88 to 99.9 wt % of water, and further comprising the following components to form an electronic cleaning composition:
   (a) 0.1 to 3 wt % of tetramethylanimonium hydroxide; and
   (b) 0 to 4 wt % of phenolic resin.

34. A product prepared by the reaction of a N,N'-bis(polyhydroxyalkyl)alkylenediamine (2):

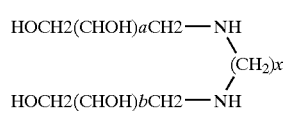

(2)

with a glycidyl ether (3):

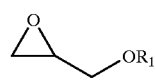

(3)

wherein a and b are integers independently selected from about 3 to about 6; x is an integer from about 1 to about 12; $R_1$ is selected from the group consisting of linear, cyclic, and branched alkyl, alkenyl, aryl, alkylaryl groups having from about $C_3$ to about $C_{30}$ atoms, including mixtures thereof; and the ratio of glycidyl ether to N,N'-bis(polyhydroxyalkyl)alkylenediamine is from about 1:1 to about 4:1.

* * * * *